United States Patent [19]

Rousset et al.

[11] Patent Number: 4,960,583

[45] Date of Patent: Oct. 2, 1990

[54] GAMMA-$FE_2O_3$/$FE_3O_4$ SPINELS

[75] Inventors: Abel Rousset, Ramonville Saint-Agne; Belaid Maachi, Segangan-Nador Maroc; Bernard Gilot; Michel Gougeon, both of Toulouse, all of France

[73] Assignee: Atochem, Puteaux, France

[21] Appl. No.: 285,422

[22] Filed: Dec. 16, 1988

[30] Foreign Application Priority Data

Dec. 16, 1987 [FR] France .................................. 87 17575

[51] Int. Cl.$^5$ ............................................. C01G 49/02
[52] U.S. Cl. .................................. 423/633; 423/213.5; 423/656
[58] Field of Search .................................... 423/633
[56] References Cited

U.S. PATENT DOCUMENTS 4,396,596  8/1983  Ogisu .................................. 423/633
4,622,281  11/1986  Imai ..................................... 423/633

Primary Examiner—Peter D. Rosenberg
Attorney, Agent, or Firm—Burns, Doane Swecker & Mathis

[57] ABSTRACT

Oxides having the spinel structure of $\gamma$-$Fe_2O_3$/$Fe_3O_4$ type, substituted by trivalent and monovalent metals, or doped with non-spinel derivatives thereof, more particularly iron/aluminum/potassium oxides well suited as dehydrogenation catalysts, e.g., for dehydrogenating ethylbenzene into styrene, are prepared by thermally decomposing mixed iron, aluminum and potassium salts, notably the oxalates thereof, in the presence of air, then reducing the product of thermal decomposition at a temperature of less than 400° C., advantageously in the presence of steam and hydrogen, and optionally oxidizing the product of reduction; oxides of $\beta$-alumina structure are also produced.

22 Claims, No Drawings

GAMMA-FE₂O₃/FE₃O₄ SPINELS

BACKGROUND OF THE INVENTION

1. Field of the Invention:

The present invention relates to a composition of matter which comprises an iron oxide of spinel structure, also containing trivalent and monovalent metals forming part of the spinel structure, and to the use of such composition as a catalyst for dehydrogenation, particularly of ethylbenzene to styrene.

This invention also relates to the preparation of such composition of matter by the decomposition of a mixed organic iron salt of said trivalent and monovalent metals, followed by a reduction in the presence of hydrogen and steam and, if appropriate, an oxidation.

2. Description of the Prior Art:

The dehydrogenation of hydrocarbons is a reaction which quite frequently is carried out on an industrial scale, for example to prepare butadiene from butene or styrene from ethylbenzene. Patent FR 2,506,294 describes a dehydrogenation catalyst consisting of iron oxide of spinel structure containing trivalent metals such as aluminum and chromium, and divalent metals such as calcium and manganese, all such metals being in the spinel structure. The spinel structure also contains lithium and may contain sodium, silver or copper. This catalyst is improved by the addition of alkali metal oxides and of vanadium oxide outside the spinel structure. The surface of a catalyst of this type does not exceed 2 m²/g.

European Patent Application No. EP 177,832 describes dehydrogenation catalysts formed by calcining oxides of iron, chromium, potassium and magnesium.

A low surface catalyst is often relatively inactive, that is to say, a large amount of it is necessary to ensure a given hourly production of dehydrogenated product, and metal oxides which do not form part of the spinel structure tend to migrate out of the catalyst and disappear.

SUMMARY OF THE INVENTION

Thus, a major object of the present invention is the provision of a novel iron oxide of spinel structure which is well suited as a dehydrogenation catalyst.

Briefly, the present invention features a composition of matter based on an oxide having the lacunar spinel structure, having a specific surface area greater than 2 m²/g, and comprising:

(a) at least one oxide of lacunar spinel structure of the γ-Fe₂O₃ type and having the formula:

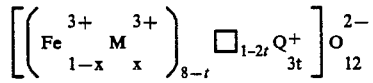

in which M denotes a trivalent metal or any mixture of such metals, Q denotes a monovalent metal or any mixture of such metals, x ranges from 0 to ⅔ and t ranges from 0 to 0.5;

(b) optionally, at least one derivative of one or more metals Q not forming part of the spinel structure and capable of being other than the metal Q of such structure.

DETAILED DESCRIPTION OF THE PREFERRED EMBODIMENTS OF THE INVENTION

More particularly according to the present invention, the term "spinel" denotes the members of a group of multiple oxides having the same crystalline structure as the specific mineral spinel MgAl₂O₄. In the formula above, the symbol

"□"

represents a vacancy in the spinel structure.

The present invention also features a composition of matter identical to the above, except that the oxide of lacunar spinel structure of the γ-Fe₂O₃ type is replaced with an oxide of spinel structure of the Fe₃O₄ type, the formula of which derives from the above.

By the formula of the oxide "derives from the above" is intended that the empirical formula contains the same metals, aside from oxygen.

The present invention also features any composition of matter which is intermediate between the two above, that is to say, the oxide of spinel structure contained in the composition is a solid solution of an oxide of spinel structure of the γ-Fe₂O₃ type and an oxide of spinel structure of the Fe₃O₄ type, both oxides having the same empirical formula, aside from oxygen.

Although it is possible to employ any trivalent metal M or combination of these metals, including the rare earths, namely, the elements having an atomic number of 57 to the atomic number 71 of the Periodic Table, preferred are chromium, aluminum or mixtures thereof. The monovalent metal Q may be selected, for example, from among the alkali metals, silver and copper. One or more metals Q may be employed. The alkali metals and preferably potassium are advantageously employed.

Although x may range from 0 to ⅔, the compositions in which x is less than 0.2 are preferred.

Although t may have any value from 0 to 0.5, the compositions in which t is less than 0.25 are preferred.

The specific surface area is that measured by the BET method (Brunauer, Emett and Teller, *J. Amer. Chem. Soc.*, 60, 309 (1938)). Compositions whose specific surface area ranges from 2 to 100 m²/g, and preferably from 3 to 30 m²/g, are advantageously employed.

Among the compositions where Q is potassium, those in which t ranges from 0 02 to 0.15 are preferred.

Among the compositions where M is aluminum, those in which x ranges from 0.05 to 0.2 are preferred.

The compositions according to the invention may optionally contain one or more derivatives of metals selected from among the metals Q and not forming part of the spinel structure. This metal, or these metals, may be different from the metal(s) Q included in the spinel structure. For example, sodium and lithium may be present in the spinel structure and potassium outside the spinel structure, or vice versa. Compositions in which potassium is present in the spinel structure and outside this structure are preferred. Advantageously, the derivatives of these metals are oxides. Potassium oxide is preferably employed.

When the compositions according to the invention are being used, the oxides outside the spinel structure may be partly or completely converted into other derivatives, for example into carbonates and bicarbonates, depending on the oxygen content of the gas phase wherein the compositions are present and on whether the carbon comes into contact with the compositions.

Similarly, depending on the gas phase in which the composition according to the invention is placed, there may be a change in the distribution of the oxides of the $\gamma$-Fe$_2$O$_3$ and Fe$_3$O$_4$ type.

The present invention also features a process for the dehydrogenation of a hydrocarbon material, wherein a composition of matter according to the invention is employed as a catalyst.

The hydrocarbon material is any material capable of losing two hydrogen atoms to form a carbon-carbon double bond. This hydrocarbon starting material may also contain a double bond and the process of the invention then makes it possible to create a second double bond in the molecule. The process of the invention is particularly useful for dehydrogenating ethylbenzene to styrene.

The present invention also features a process for the preparation of the subject compositions.

The process is characterized in that:

(a) mixed organic salts of the metals M and Q and based on iron are decomposed in the presence of air or of a gas containing oxygen, until oxides of the metals M, Q and of iron are produced;

(b) such metal oxides are reduced until a composition containing the said metal oxides in the form of a spinel of the Fe$_3$O$_4$ type is obtained;

(c) if desired, a total or partial oxidation of the compositions obtained in (b) is carried out until a composition is obtained containing said metal oxides in the form of a spinel of the Fe$_3$O$_4$ type and said metal oxides in the form of a lacunar spinel of the $\gamma$-Fe$_2$O$_3$ type, the formula of which is derived from those preceding, and the two oxides of the $\gamma$-Fe$_2$O$_3$ and Fe$_3$O$_4$ type form a solid solution.

By the expression "mixed salt" is intended a salt in which the metals forming part of the composition of the oxide are already combined on an atomic scale by exchange of bonds or by intergrowth between the single salts, given the structural isomorphism between the single salts of these metals.

The mixed salts of the metals M, Q and of iron may be acetates, formates, citrates, oxalates or lactates and, generally, any material forming salts of the metals M, Q and of iron and which are mutually soluble in water or alcohols or ketones or ethers.

It is preferable, however, to employ salts prepared from oxalic acid.

When the salts are being decomposed, the rate of temperature increase is preferably less than 300.C/h to avoid a transient reduction to metallic iron and the demixing of the resulting oxides.

Although step (a) may be carried out over a wide range of temperature, it is preferably performed at a temperature of from 250 to 500° C.

The reduction in step (b) is advantageously carried out in the presence of a mixture consisting essentially of steam and hydrogen, or a mixture of carbon monoxide and carbon dioxide.

Step (b) is preferably carried out at a temperature of from 250° to 800° C.

Another preferred embodiment of step (b) entails carrying out the reduction at a temperature of from 350° to 380° C. in the presence of a mixture of steam and hydrogen.

To prepare the compositions according to the invention containing various metals in the desired proportions, it suffices to prepare mixed salts containing these metals in the same proportions.

An alternative embodiment of the process of the invention enables ferrites of the $\beta$-alumina structure to be prepared. Although in the process immediately above described, amorphous oxides are obtained at the end of step (a), it has now been found that oxides of $\beta$-alumina structure are obtained when step (a) is carried out at high temperature.

The invention thus circumscribes a process for the preparation of oxides of the empirical formula:

$$K_{1+z}Fe_{11-x-y}Al_xCr_yO_{17}$$

and of $\beta$-alumina structure; in which:

x+y ranges from 0 to 11;

x and y are positive numbers;

z ranges from 0 to 2 and represents the departure from stoichiometry, comprising decomposing mixed organic salts of Fe, Al, Cr and K at a temperature at least equal to 550 C, until the oxide of $\beta$-alumina structure is produced.

The invention is particularly useful for the preparation of oxides having a specific surface area (BET surface) of up to 100 m$^2$/g and advantageously ranging from 10 to 60 m$^2$/g. The same mixed salts as above are advantageously employed, and the oxalates are preferred. It suffices to prepare the mixed salts using the metal proportions of the required empirical formula.

The decomposition temperature is usually below 1,200° C. and preferably ranges from 700° to 1,000° C., and the duration of this decomposition is on the order of 30 minutes to 3 hours.

In order to further illustrate the present invention and the advantages thereof, the following specific examples are given, it being understood that same are intended only as illustrative and in nowise limitative.

EXAMPLES

Examples 1 to 7 illustrate the oxides of spinel structure:

$$\gamma\text{-Fe}_2\text{O}_3/\text{Fe}_3\text{O}_4,$$

and Example 8 illustrates the oxide of $\beta$-alumina structure.

1. Preparation of the Mixed Salts

The mixed salts of the general formula:

$$[(NH_4)_{1-x}K_x]_3 (Fe_{1-y-y'}Al_yCr_{y'}) (C_2O_4)_3 \cdot 3H$$

in which x and y+y' ranged from 0 to 1, were prepared by syncrystallization of the simple oxalates selected from among:

$$(NH_4)_3Fe(C_2O_4)_3 \cdot 3H_2O; K_3Fe(C_2O_4)_3 \cdot 3H_2O;$$

$$(NH_4)_3Al(C_2O_4)_3 \cdot 3H_2O; K_3Al(C_2O_4)_3 \cdot 3H_2O;$$

$$(NH_4)_3Cr(C_2O_4)_3 \cdot 3H_2O; \text{ and } K_3Cr(C_2O_4)_3 \cdot 3H_2O.$$

(a) Mixed Oxalates (Operating Procedure 1):

a grams of iron ammonium oxalate, b grams of iron potassium oxalate, c grams of aluminum ammonium oxalate, d grams of potassium aluminum oxalate, e grams of chromium ammonium oxalate and f grams of chromium potassium oxalate were dissolved in 2 l of deionized water. The mixture was then heated under stirring to a temperature of 70° C to concentrate the solution. When the recrystallization commenced, the heating was stopped and the solution cooled. The syncrystallization of the oxalates was continued on a sand bath at 40.C until the solution had completely evaporated. The values of a, b, c, d, e and f for the preparation of 100 g of each of the various oxides are reported in the Table which follows.

(b) Simple Oxalates Not Available Commercially (Operating Procedure 2):

The oxalate $(NH_4)_3M(C_2O_4)_3 \cdot 3H_2O$ was prepared by gradual addition of freshly prepared hydroxide of the trivalent metal M to an aqueous solution of oxalic acid and of ammonium oxalate, maintained at 50 C. The respective proportions of hydroxide, of oxalic acid and of ammonium oxalate employed were those corresponding to the stoichiometry of the reaction The solution obtained was then concentrated to initiate the crystallization. The latter was carried out on a sand bath at 40.C until the solution had completely evaporated.

Operating Procedure 3

The oxalate $K_3M(C_2O_4)_3 \cdot 3H_2O$ was prepared according to Operating Procedure 2, ammonium oxalate being replaced with potassium oxalate.

2. Preparations of the Oxides

Operating Procedure 4; Example 1

The mixed iron-ammonium-potassium salt was decomposed by pyrolysis in air at 450 C for 1 hour. The rate of temperature increase to 450.C was 150° C./h. The oxides then obtained, of high specific surface area, were then reduced at 350 C for 4 hours using a 70% hydrogen/30% steam gaseous mixture. The resulting oxide was predominantly a spinel phase of $Fe_3O_4$ type.

Operating Procedure 5; Examples 2 and 3

The pyrolysis of the iron-ammonium-potassium salt at 450° C for 1 hour and the reduction at 350 C for 4 hours were carried out following Operating Procedure 4. These were followed by an air oxidation at 400° C for 1 hour. The rate of temperature increase to 400° C. was 150 C/h. The oxide obtained was chiefly a lacunar spinel phase of the $\gamma$-$Fe_2O_3$ type.

Operating Procedure 6; Example 4

The pyrolysis of the iron-ammonium-potassium salt at 450° C for 1 hour and the reduction at 350 C for 4 hours were carried out following Operating Procedure 4. These were followed by an air oxidation at 130 C for 2 hours. The oxide obtained contained predominantly a solid solution of a composition intermediate between the substituted magnetite and the corresponding lacunar spinel.

Operating Procedure 7; Examples 5, 6 and 7

The mixed iron-aluminum-potassium-ammonium or iron-chromium-potassium-ammonium salt was decomposed by pyrolysis in air at 400.C for 1 hour. The rate of temperature increase to 400° C was 150 C/h. The oxides then obtained were amorphous. They were next reduced at 370° C for 5 hours with a gaseous mixture containing 60% of hydrogen and 40% of steam, were quenched and were finally oxidized at 400.C for 1 hour, with a rate of temperature increase to 400 C of 150° C./h. The oxide obtained was predominantly of lacunar spinel phase.

Operating Procedure 8; Example 8

The iron-potassium-ammonium salt was pyrolyzed at 950° C. for 1 hour, the rate of temperature increase was 150° C./h. The resulting oxide, in the case of a weight content of potassium in the oxide of 6 to 8%, was a potassium ferrite of the $\beta$-alumina type, which formed from 600 C and higher.

3. Measurement of Catalytic Activity (Ethylbenzene dehydrogenation Reaction)

The catalytic activities of the compositions according to the invention were measured at 550 C at atmospheric pressure in the case of a partial pressure of ethylbenzene equal to $7.5 \times 10^3$ Pa and a partial pressure of steam/partial pressure of ethylbenzene ratio equal to 20. The flow rate of ethylbenzene was $10^{-5}$ moles per second per gram of catalyst.

The results are reported in the Table which follows, in the form of the ratio of the mass activity of the oxide to the mass activity of a catalyst, measured under the same experimental conditions.

The existing catalyst, used as a reference, was obtained by calcining a mixture of 93% of $Fe_2O_3$, 5% of $Cr_2O_3$ and 2% of KOH, by weight.

TABLE

| EXAMPLES | MIXED PRECURSOR (in grams) a / b / c / d | COMPOSITION OF THE OXIDE Composition of the spinel phase | % $K_2O$ 2* | Crystal parameter A° 3* | Specific surface $m^2/g$ 4* | Oxidation temperature °C. 5* | Conversion temperature 6* | Activity 7* |
|---|---|---|---|---|---|---|---|---|
| 2 | 517 / 8.38 / / | $K^+_{0.247}Fe^{3+}_{7.948}\square_{0.835}O^{2-}_{12}$ | ~0.6% | 8.35 | 23 | — | 720 | 12 |
| 1 | 517 / 8.38 / / | $K^+_{0.272}Fe^{3+}_{6.272}Fe^{2+}_{2.455}O^{2-}_{12}$ | ~0.6% | 8.40 | 24.5 | 210 | — | 12.5 |
| 4 | 517 / 8.38 / / | $K^+_{0.262}Fe^{3+}_{6.969}Fe^{2+}_{1.415}\square_{0.354}O^{2-}_{12}$ | ~0.6% | 8.375 | 24 | — | 720 | 2.5 |
| 3 | 456 / 33.5 / / | $K^+_{0.314}Fe^{3+}_{7.895}\square_{0.791}O^{2-}_{12}$ | ~7.3% | 8.40 | 15 | — | 700 | 5.6 |
| 5 | 495 / / 10.64 / 15.98 | $K^+_{0.478}Fe^{3+}_{7.449}Al_{0.392}\square_{0.682}O^{2-}_{12}$ | ~1.3% | 8.33 | 33 | — | 735 | 6 |
| 6 | 296 / / 25.1 / 263 | $K^+_{0.423}Fe^{3+}_{4.165}Al^{3+}_{3.694}\square_{0.718}O^{2-}_{12}$ | ~3% | 8.31 | 21 | — | 800 | 2.6 |

TABLE-continued

| EXAMPLES | MIXED PRECURSOR (in grams) | | | | COMPOSITION OF THE OXIDE | | Crystal parameter A° 3* | Specific surface m²/g 4* | Oxidation temperature °C. 5* | Conversion temperature 6* | Activity 7* |
|---|---|---|---|---|---|---|---|---|---|---|---|
| | | | | | Composition of the spinel phase | % K₂O 2* | | | | | |
| | a | b | e | f | | | | | | | |
| 7 | 465 | | 39.46 | 15.03 | $K^+_{0.412}Fe^{3+}_{7.07}Cr^{3+}_{0.786}\square_{0.725}O^{2-}_{12}$ | ~1% | 8.34 → | 30 | — | 725 | 10 |
| | a | b | c | d | Potassium ferrite | | | | | | |
| 8 | 453 | | 19.7 | 31.97 | $K_{1.8}(Fe_{9.9}Al_{0.1})_{11}O_{17}$ | ~0% | a = 5.92 → c = 23.4 | 12.4 | — | — | 3 |

1* Weights of the simple oxalates employed for the preparation of 100 g of oxide.
2* % K₂O out of the spinel phase relative to the total mass of oxide (in most cases in the form of carbonates K₂CO₃.3/2H₂O, KHCO₃).
3* Of the spinel phase.
4* Of the oxide, determined by the B.E.T. method.
5* For the magnetites, determined by differential thermal analysis, rate of heat increase = 10° C./min.
6* Lacunar spinel - oxide of corundum structure conversion. DTA 10° C./min.
7* Ratio of the mass activity of the oxide/activity of an existing catalyst.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A composition of matter based on an oxide having the lacunar spinel structure, having a specific surface area greater than 2 m²/g and comprising:
  (a) at least one oxide of lacunar spinel structure of the γ-Fe₂O₃ type and having the formula:

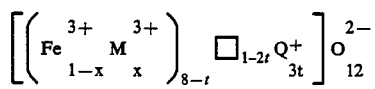

in which M is a trivalent metal or any mixture of trivalent metals, Q is a monovalent metal or any mixture of monovalent metals, x ranges from 0 to ⅔, t ranges from 0 to 0.5, and $$\square$$

represents a vacancy in the spinel structure.

2. The composition of matter as defined by claim 1, further comprising:
  (b) at least one derivative of one or more metals Q which do not constitute part of the spinel structure and which may be other than the metal Q of such structure.

3. The composition of matter as defined by claim 1, wherein the oxide of lacunar spinel structure of γ-Fe₂O₃ type is replaced with an oxide of spinel structure of the Fe₃O₄ type, the formula of which is derived from the former.

4. The composition of matter as defined by claim 1, wherein the oxide of lacunar spinel structure of γ-Fe₂O₃ type is partially replaced with an oxide of spinel structure of the Fe₃O₄ type, the formula of which is derived from the former, and the two oxides of γ-Fe₂O₃ and Fe₃O₄ type forming a solid solution.

5. The composition of matter as defined by claim 1, wherein x is less than 0.2.

6. The composition of matter as defined by claim 1, wherein t is less than 0.25.

7. The composition of matter as defined by claim 1, having a specific surface area of from 2 to 100 m²/g.

8. The composition of matter as defined by claim 1, wherein M comprises aluminum.

9. The composition of matter as defined by claim 8, wherein x ranges from 0.05 to 0.2.

10. The composition of matter as defined by claim 1, wherein Q comprises potassium.

11. The composition of matter as defined by claim 10, wherein t ranges from 0.02 to 0.15.

12. The composition of matter as defined by claim 10, further comprising non-spinel potassium oxide.

13. In a process for the catalytic dehydrogenation of a hydrocarbon, the improvement which comprises, as the catalyst therefor, the composition of matter as defined by claim 1.

14. The process as defined by claim 13, comprising the dehydrogenation of ethylbenzene to styrene.

15. A process for the preparation of the composition of matter as defined by claim 1, comprising:
  (a) decomposing mixed organic salts of the metals M and Q, based on iron, in the presence of air or a gas containing oxygen, until oxides of the metals M, Q and of iron are produced;
  (b) reducing such metal oxides until a composition containing said metal oxides in the form of a spinel of Fe₃O₄ type is obtained.

16. The process as defined by claim 15, further comprising (c) completely or partially oxidizing the product of step (b) until a composition is produced containing said metal oxides in the form of a spinel of Fe₃O₄ type and also said metal oxides in the form of a lacunar spinel of γ-Fe₂O₃ type, the formula of which is derived from the former, and wherein the two oxides of γ-Fe₂O₃ and Fe₃O₄ type form a solid solution.

17. The process as defined by claim 15, wherein step (a) is carried out at a temperature of from 250 to 500° C.

18. The process as defined by claim 15, wherein step (b) is carried out in the presence of a mixture of steam and hydrogen, or of carbon monoxide and carbon dioxide.

19. The process as defined by claim 15, wherein step (b) is carried out at a temperature of from 250 to 800° C.

20. The process as defined by claim 15, said organic salts comprising oxalates.

21. The process as defined by claim 15, wherein step (b) is carried out at a temperature of from 350 to 380° C. in the presence of a mixture of steam and hydrogen.

22. A process for the preparation of oxides of the formula:

$K_{1+z}Fe_{11-x-y}Al_xCr_yO_{17}$ and of β-alumina structure, in which x+y ranges from 0 to 11, x and y are positive, and z ranges from 0 to 2 and represents the departure from stoichiometry, comprising decomposing mixed organic salts of Fe, Al, Cr and K at a temperature of at least 550 C until the oxide of β-alumina structure is produced.

* * * * *

UNITED STATES PATENT AND TRADEMARK OFFICE
CERTIFICATE OF CORRECTION

PATENT NO. : 4,960,583
DATED : October 2, 1990
INVENTOR(S) : Abel Rousset et al

It is certified that error appears in the above-identified patent and that said Letters Patent is hereby corrected as shown below:

Col. 7, line 9, in the Table, below the heading "Composition of the Spinel Phase", delete "$K^+_{0.412} Fe^{3+}_{7.07} Cr^{3+}_{0.786} 0.725 O^{2-}_{12}$"

and insert

--- $K^+_{0.412} Fe^{3+}_{7.07} Cr^{3+}_{0.786}\ \square\ 0.725 O^{2-}_{12}$ ---.

Signed and Sealed this

Third Day of November, 1992

Attest:

DOUGLAS B. COMER

*Attesting Officer*  *Acting Commissioner of Patents and Trademarks*